(12) United States Patent
Braman et al.

(10) Patent No.: US 10,662,424 B2
(45) Date of Patent: May 26, 2020

(54) MOLECULAR FABRICATION

(71) Applicant: Agilent Technologies, Inc., Loveland, CO (US)

(72) Inventors: Jeffrey Carl Braman, Carlsbad, CA (US); Peter James Sheffield, Vista, CA (US); Gavin Fischer, Santa Clara, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 198 days.

(21) Appl. No.: 14/649,493

(22) PCT Filed: Oct. 2, 2013

(86) PCT No.: PCT/US2013/063146
§ 371 (c)(1),
(2) Date: Jun. 3, 2015

(87) PCT Pub. No.: WO2014/088693
PCT Pub. Date: Jun. 12, 2014

(65) Prior Publication Data
US 2016/0215283 A1    Jul. 28, 2016

Related U.S. Application Data

(60) Provisional application No. 61/734,258, filed on Dec. 6, 2012.

(51) Int. Cl.
| | | |
|---|---|---|
| C12N 15/10 | (2006.01) | |
| C12N 15/66 | (2006.01) | |
| C12N 15/64 | (2006.01) | |
| C12N 15/70 | (2006.01) | |

(52) U.S. Cl.
CPC ......... *C12N 15/1082* (2013.01); *C12N 15/10* (2013.01); *C12N 15/1027* (2013.01); *C12N 15/64* (2013.01); *C12N 15/66* (2013.01); *C12N 15/70* (2013.01)

(58) Field of Classification Search
None
See application file for complete search history.

(56) References Cited

U.S. PATENT DOCUMENTS 6,165,793 A * 12/2000 Stemmer .......... C07K 14/43595
435/440
2004/0161752 A1   8/2004 Jarrell et al.

FOREIGN PATENT DOCUMENTS

| | | |
|---|---|---|
| CN | 1145641 A | 3/1997 |
| JP | 2000500981 A | 2/2000 |
| JP | 2000512852 A | 10/2000 |
| JP | 2002538763 A | 11/2002 |
| JP | 2011512140 A | 4/2011 |
| WO | 9720078 | 6/1997 |
| WO | 9720078 A1 | 6/1997 |
| WO | WO199720078 | 6/1997 |
| WO | 9748716 | 12/1997 |
| WO | 9748716 A1 | 12/1997 |
| WO | WO 02/08408 | 1/2002 |
| WO | 2009103027 A2 | 8/2009 |

OTHER PUBLICATIONS

Berger, et al., "Phoenix Mutagenesis: One-Step Reassembly of Multiply Cleaved Plasmids with Mixtures of Mutant and Wild-Type Fragments", Analytical Biochemistry, 214, 571-579 (1993).
Fernandes, et al., "Seamless cloning and domain swapping of synthetic and complex DNA", Analytical Biochemistry 385 (2009) 171-173.
Kikuchi, et al., "Novel family shuffling methods for the in vitro evolution of enzymes", Gene 236 ( 1999) 159-167.
Lu, Quinn, "Seamless cloning and gene fusion", Trends in Biotechnology, (2005) vol. 23, No. 4.
McDaniel, et al., "Recursive Directional Ligation by Plasmid Reconstruction Allows Rapid and Seamless Cloning of Oligomeric Genes", Biomacromo/ecules, 2010, 11. 944-952.
Padgett, et al., "Creating seamless junctions independent of restriction sites in PCR cloning", Gene. 168, (1996) 31-35.
Weber, et al., "A Modular Cloning System for Standardized Assembly of Multigene Constructs", PLoS ONE, 2011, 6(2): e16765.
Werner, "Fast track assembly of multigene constructs using Golden Gate cloning and the MoClo system", Bioengineered Bugs, 2012, 3(1): 38-43.
Zhu, et al., "In-Fusion™ Assembly: Seamless Engineering of Multidomain Fusion Proteins, Modular Vectors, and Mutations", BioTechniques, vol. 43, No. 3, Sep. 2007, 354-359.
Garforth, et al., "Structure-Specific DNA Binding by Bacteriophage T5 5'→3' Exonuclease", Nucleic Acids Research, vol. 25, No. 19, 1997, 3801-3807.
Sleight, et al., "In-Fusion Biobrick Assembly and Re-Engineering", Nucleic Acids Research; vol. 38, No. 8, 2010, 2624-2636.

* cited by examiner

*Primary Examiner* — Mindy G Brown

(57) ABSTRACT

Provided herein is a method for fabricating transformable or transfectable molecules that includes an assembly reaction containing a variety of pre-made cassettes possessing ends that hybridize to one another, transforming or transfecting said molecules into a desired host cell and then selecting a transformed/transfected host cell containing plasmid molecules composed of said the cassettes. A kit for performing the method is also provided.

10 Claims, 15 Drawing Sheets

MOLECULAR FABRICATION

BACKGROUND

Synthetic biology is a relatively new area of research employing both biochemical and engineering sciences for the purpose of designing and constructing new cellular functions and systems not found in nature. To accomplish these ambitious goals, simplifying the design and use of molecular cloning tools is of paramount importance.

SUMMARY

Provided herein is a method for fabricating a variety of plasmids by assembling various pre-made cassettes containing complementary ends that hybridize to one another resulting in the production of molecules that can be introduced into host cells. Selecting host cells with desired properties that are composed of cassette containing plasmid molecules thus represents a significant improvement over existing molecular cloning tools. A kit for performing the method is also provided.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
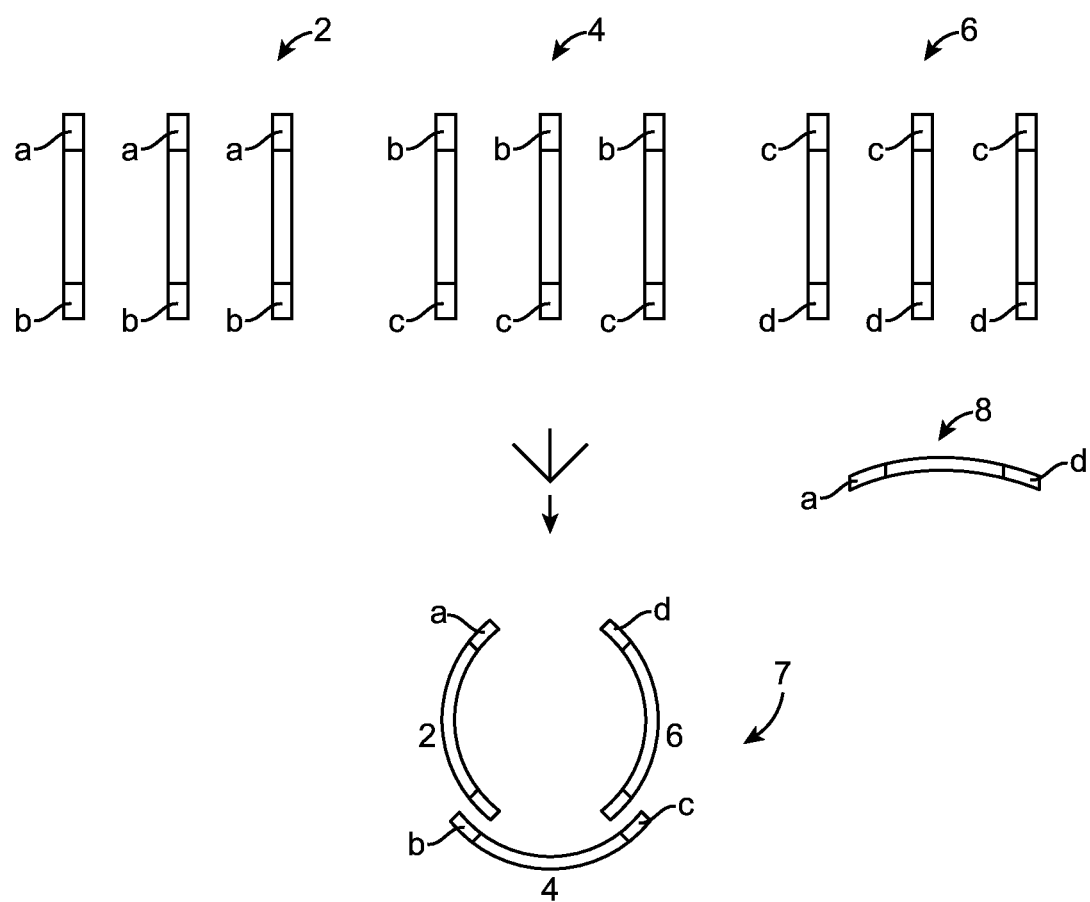
FIG. 1 schematically illustrates some of the features of the components used in the method.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a cassette" refers to one or two or more cassettes, i.e., a single cassette and multiple (at least two) cassettes. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides from about 2 to 200 nucleotides, up to 500 nucleotides in length. Oligonucleotides may be synthetic or may be made enzymatically, and, in some embodiments, are 4 to 150 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51 to 60, 61 to 70, 71 to 80, 80 to 100, 100 to 150 or 150 to 200 nucleotides in length, for example.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long enough to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15 to 25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "Selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 µg/mL denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and [$Na^+$] is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "free in solution," as used here, describes a molecule, such as a polynucleotide, that is not bound or tethered to another molecule.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "ligating", as used herein, refers to the enzymatically catalyzed joining of the terminal nucleotide at the 5' end of a first DNA molecule to the terminal nucleotide at the 3' end of a second DNA molecule.

The term "covalently linking" refers to the production of a covalent linkage between two separate molecules, e.g., Ligating is a type of covalent linking.

The terms "set" and "plurality" are used interchangeably to refer to a population that contains at least 2 members. In certain cases (and depending on the context), a plurality or a set may have at least 3, at least 4, at least 5, at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "digesting" is intended to indicate a process by which a nucleic acid is cleaved by a restriction enzyme. In order to digest a nucleic acid, a restriction enzyme and a nucleic acid containing a recognition site for the restriction enzyme are contacted under conditions suitable for the restriction enzyme to work. Conditions suitable for activity of commercially available restriction enzymes are known, and supplied with those enzymes upon purchase.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "extending", as used herein, refers to the extension of a primer by the addition of nucleotides using a polymerase. If a primer that is annealed to a nucleic acid is extended, the nucleic acid acts as a template for the extension reaction.

The term "do not hybridize to each other", as used herein in the context of nucleic acids that do not hybridize to each other, refers to sequences that have been designed so that they do not anneal to one another under stringent conditions. Exemplary sequences that do not hybridize with each other (which may be called "sequence tokens" in certain publications), are described in, e.g., US20070259357 and Brenner et al (Proc. Natl. Acad. Sci. 1992 89:5381-3), which are incorporated by reference herein.

The terms "that hybridize to each other", as used herein in the context of nucleic acids that hybridize to one other, refers to sequences that been designed so that they anneal to one another under stringent conditions.

As used herein, the term "flap cleavage reaction" refers to a reaction in which a substrate is cleaved in an overlap-dependent manner by a flap endonuclease to release a flap. The principles of flap assays are well known and described in, e.g., Lyamichev et al. (Nat. Biotechnol. 1999 17:292-296), Ryan et al (Mol. Diagn. 1999 4:135-44) and Allawi et al (J Clin Microbiol. 2006 44: 3443-3447).

The term "flap endonuclease" or "FEN" for short, as used herein, refers to a class of nucleolytic enzymes that act as structure specific endonucleases on DNA structures with a duplex containing a single stranded 5' overhang, or "flap", on one of the strands that is displaced by another strand of nucleic acid, i.e., such that there are overlapping nucleotides at the junction between the single and double-stranded DNA. FENs catalyze hydrolytic cleavage of the phosphodiester bond at the junction of single and double stranded DNA, releasing the overhang, or the flap. Flap endonucleases are reviewed by Ceska and Savers (*Trends Biochem. Sci.* 1998 23:331-336) and Liu et al (*Annu. Rev. Biochem.* 2004 73: 589-615). FENs may be individual enzymes, multi-subunit enzymes, or may exist as an activity of another enzyme or protein complex, e.g., a DNA polymerase. A flap endonuclease may be thermostable.

The term "flap endonuclease substrate", as used herein, refers to a nucleic acid complex that can be cleaved by a flap endonuclease to produce cleavage products. Such complex contains a single stranded 5' overhang (a "flap") that has been displaced by another strand in a duplex.

The term "cassette" refers to a double stranded DNA molecule that, when present in a construct in an appropriate context, is functional or encodes a product that is functional. Promoters, terminators, origins of replication and coding sequences are examples of cassettes. Cassettes are modular in the sense that they are functional when they are moved into an equivalent context in one or more different constructs. For example, a promoter (which is a type of cassette) can be moved from one construct to another and can drive the expression of different coding sequences. Likewise, coding sequence can be transcribed by various upstream promoters. A cassette can be made by PCR or synthesized by any other method. In some but not all cases a cassette can contain more than one functional element in operable linkage. For example, a promoter cassette may also contain a 5' untranslated region, a ribosome binding site and a terminator in addition to the sequence of interest.

The term "coding sequence" refers to a sequence that encodes a polypeptide and to a sequence that encodes a functional RNA, e.g., a regulatory RNA.

The term "set" within the context of a "set of cassettes" refers to a group of at least two cassettes (e.g., 2, 3, 4, 5, or 6 or more cassettes) that are functionally related. For example, one set of cassettes may contain different promoters, another set of cassettes may contain different terminators, another set of cassettes may contain different selectable markers, and a further set of cassettes may contain different origins of replication, and so on.

The term "set of origin of replication cassettes" refers to cassettes that contain origins of replication, where each cassette contains a single origin of replication and the different origin of replication cassettes contain different origins of replication. A set of origin of replication cassettes may in certain cases contain one or more of a bacterial origin of replication cassette (which may result in a high or low copy number), a yeast origin of replication cassette and a mammalian origin of replication cassette.

The term "set of selectable marker cassettes" refers to cassettes that encode selectable markers (i.e., proteins that can be used to select cells that contain the protein), where each cassette encodes a single selectable marker and the different selectable marker cassettes contain different selectable markers. A selectable marker of replication cassettes may contain one or more bacterial selectable marker cassettes, one or more yeast selectable marker cassettes and/or one or more mammalian selectable marker cassettes. Exemplary selectable markers encode proteins that provide resistance to antibiotics such as ampicillin, for example.

The term "target cassette" refers to a cassette that comprises a sequence of interest. In some cases the target cassette encodes a product (e.g., a protein or RNA product) that is to be expressed in a cell, e.g., by operably linking the target cassette to at least a promoter. In this context, the term "sequence of interest" is intended to include a sequence or series of sequences of interest. A single sequence of interest may code for a specific protein desired for large scale expression and purification. A series of sequences may result in expression of a number of proteins that, in certain cases, may convert a starting substrate into a final product of interest, such as a fine chemical intermediate, an antibiotic or derivative thereof, a portion of or an entire anabolic or catabolic pathway, or a specific transcriptional circuit, as examples.

The term "set of functional cassettes" refers to cassettes that are functionally related. As will be described in greater detail below, types of functional cassette include, but are not limited to: promoter cassettes, terminator cassettes, shuttle selectable marker cassettes (i.e., a second cassette that can be added to a plasmid in addition to a first origin of replication cassette to allow the plasmid to replicate in another species), and protein coding regions including cassettes that encode N-terminal purification tags, C-terminal purification tags, protein expression enhancers, counter selectable markers and reporter proteins, etc.

The term "vessel" refers to any type of container, e.g., a tube or vial. In this context, the different wells of a multi-well plate (e.g., a 96-well plate) should be considered different vessels.

The term "selecting" refers to the act of identifying an item from a plurality, and then using the identified item. "Selecting" refers to the physical act of obtaining an item.

The term "cassettes comprise ends that hybridize with one another to produce a circular product" refers to a collection of cassettes that contain ends that are designed to hybridize with each other in a way that provides a circular DNA molecule that contains the collection of cassettes.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter).

The terms "transformed" and "transfected" refer to the introduction of exogenous nucleic acid into a host cell to yield a plasmid or other vector that autonomously replicates in the host cell. Electroporation, heat shock, viral infection, and chemical (e.g., liposome-mediated) means, as well as other means (e.g., injection, dipping, etc., for plant) are exemplary ways in which a cell can be transformed or transfected by an exogenous nucleic acid.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Prior to describing the method, a general description of some of the components used in the method is provided with reference to FIG. 1. FIG. 1 shows a set of origin of replication cassettes 2, a set of selectable marker cassettes 4, and a set of functional cassettes 6. As shown, each cassette contains a first sequence of nucleotides at one end and a second sequence of nucleotides at the other end where the sequences at the first and second ends are different from one another (e.g., a and b, b and c, or c and d). In some embodiments the end sequences can be in the range of 4 to 100 base pairs, e.g., 12 to 50 or 15 to 30 base pairs, in length and should not hybridize to one another or to any non-end sequences in any of the cassettes (except when specific hybridization is desired). In certain cases, the end sequences may contain other features such as restriction sites, primer binding sites and/or T7/T3 promoters that may facilitate future manipulations after several cassettes have been assembled. In particular cases, the end sequences are $T_m$-matched, where the term "$T_m$-matched" refers to a set of sequences that have $T_m$'s that are within a defined range, e.g., within 5° C. or 10° C. of one another. Also as shown, within each set of cassettes, all of the cassettes have the same sequence at one end and a different but same sequence at the other. For example, all of the cassettes in the set of origin of replication cassettes 2 have sequence a at one end, and sequence b at the other. Likewise, all of the cassettes in the set of selectable marker cassettes 4 have sequence b at one end, and sequence c at the other, and all of the cassettes in the set of functional cassettes 6 have sequence c at one end, and sequence d at the other. As illustrated, the ends of the cassettes are designed so that one cassette hybridizes to another to produce a chain of cassettes 7. The ends of the chain of cassettes are compatible with the ends of a target cassette 8 that comprises a sequence of interest. In the illustrative example shown in FIG. 1, the ends of the target cassette contain sequences a and d, which hybridize with the ends of the chain of cassettes (which also contain sequences a and d. When the ends of all of the cassettes are hybridized together, a circular product is produced. The general principles shown in FIG. 1 can be expanded to include more cassettes (e.g., a total of 4, 5, 6, 7, 8, 9 or 10 or more cassettes). In any one assembly, each end of a cassette hybridizes with only one end of a different cassette. As would be readily apparent, the order of the cassettes may be different to that shown in any of the figures.

Figure 2:
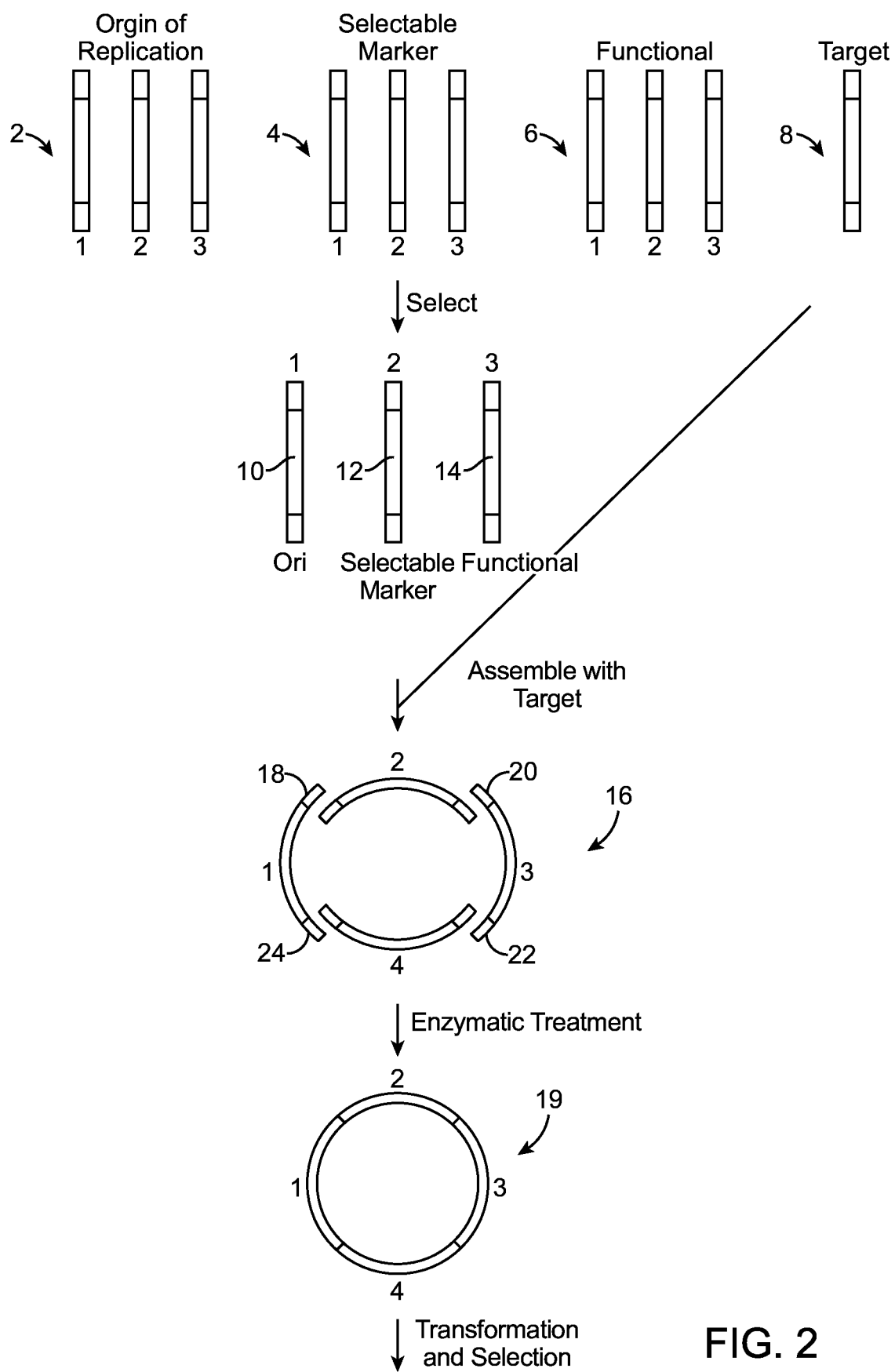
FIG. 2 schematically illustrates one implementation of the method.

With reference to FIG. 2, one embodiment of the method involves obtaining a set of origin of replication cassettes 2, a set of selectable marker cassettes 4, one or two or more sets of functional cassettes 6, and a target cassette 8 that comprises a sequence of interest; where the cassettes in each of the sets are in different vessels. As shown in this example, each set of cassettes contains three different cassettes. However, in practice, each set of cassettes may independently contain 2, 3, 4, 5, 6, 7, 8, 9 or 10 or more cassettes. The next step of the method involves selecting an origin of replication cassette, a selectable marker cassette, and one or two or more functional cassettes. In the embodiment shown, a single origin of replication 10, a single selectable marker 12 and a single functional cassette 14 are selected. In certain embodiments (and as will be discussed in greater detail below) two or more different sets of functional cassettes (e.g., one set of promoter cassettes and one set of purification cassettes) may be employed in the method. The next step of the method involves assembling the selected cassettes with the target cassette, wherein the cassettes comprise ends that hybridize with one another to produce a circular product 16. In other words, the sequences at the ends of cassettes are designed to hybridize to one another such that a circular chain of cassettes is produced in which each cassette is hybridized with two other cassettes, one at each end. In the embodiment shown in FIG. 2, four cassettes are assembled to produce the circular product 16, which requires four different sequences at the ends of the cassettes (18, 20, 22 and 24). In this step, the assembly may in certain cases involve combining the selected cassettes with the target cassette in a single vessel, adding one or more assembly proteins, heating the product so that at least the ends of the cassettes denature, and then cooling the product so that the ends of the cassettes hybridize to one another and allowing the assembly protein(s) to perform their proper function(s). A wide variety of proteins may be used for the assembly. In some embodiments, the assembly step may use a polymerase, a "flap-endonuclease" (FEN), a ligase, or a polymerase enhancing factor (PEF). These proteins may be used on their own or in combination with other enzymes. In certain cases the proteins may be used in combination with one another. For example, in certain cases polymerase and FEN; polymerase and ligase; polymerase and PEF; polymerase, FEN and ligase; polymerase, FEN and PEF; polymerase, ligase and PEF; or polymerase, FEN, ligase and PEF may be used. In certain cases, the protein used may be thermostable. In some embodiments, the circular product may be subjected to thermocycling assembly conditions to extend the 3' ends of DNA molecules in any one cassette using the adjoining cassettes as a template. In many embodiments the assembly reaction does not employ restriction enzymes, adaptor ligations and does not involve joining of blunt ended cassette assembled products.

As will be discussed in greater detail below, the method may be implemented in a variety of different ways. In one exemplary embodiment, a vector that contains one or more target cassette(s), a selectable marker cassette, an origin of replication cassette, a shuttle cassette, and a functional cassette is assembled, where the origin of replication cassette allows the plasmid to replicate in one species (e.g., *E. coli*), and the shuttle cassette allows the same plasmid to replicate in another species cells (e.g., yeast or mammalian cells, for example).

The method comprises transforming a host cell (e.g., a bacterial host cell such as *E. coli*) with the enzymatically treated product 19. In general terms, the selectable marker cassette and the origin of replication cassettes are selected so as to be compatible with the host cell used (i.e., so that once assembled into a plasmid in vivo they survive antibiotic treatment and can be replicated in the host cell). The exact configuration of the ends of the assembled cassettes in the enzymatically treated product 19 are determined by which enzymes are used to treat the circular product 16. For example, in embodiments in which the circular product is treated with a flap endonuclease, the enzymatically treated product 19 may be completely double stranded and in certain cases may contain single stranded nicks between the ends of the various cassettes. In other embodiments (e.g., if a polymerase is used for assembly), then the ends of the cassettes will be extended using a neighboring cassette as a template. Other structures are possible depending on which enzymes are used. The next step of the method may involve selecting a transformed host cell that comprises a plasmid that comprises the one or two or more selected functional cassettes, the target cassette(s), the origin of replication cassette and the selectable marker cassette. This step may be done by any convenient method, e.g., as one may screen cells that contain a plasmid made by conventional cloning. For example, in one embodiment, the enzymatically treated product 19 may be directly transformed into a bacterial, yeast or mammalian host cell, and transformed cells are selected using an agent that selects for cells containing the selectable marker encoded by the selectable marker cassette. A further round of screening may be performed by PCR screening of colonies, or by purifying plasmid DNA using a "mini-prep" procedure followed by restriction enzyme digestion, as needed.

As will be described in greater detail below, the method may be implemented in a variety of different ways depending on the desired outcome. In some embodiments the one or two or more functional cassettes are selected from a set of promoter cassettes, a set of N-terminal purification tag cassettes, a set of C-terminal purification tag cassettes, a set of shuttle origin of replication cassettes, a set of terminator cassettes, a set of protein expression enhancer cassettes; and a set of shuttle selectable marker cassettes. A user of this method should be able to make several expression cassettes that all contain the same target gene sequence(s) fused to numerous solubility enhancing tags and/or purification tags (such as GST, MBP and NusA, among many others) under the control of a variety of different promoters (prokaryotic and eukaryotic) and a vector backbone that contains an origin of replication and selectable marker that allow the resultant plasmid to function properly in the desired host species. In one embodiment, this type of vector construction method allows for a way to rapidly screen for the best host (prokaryotic or eukaryotic), the best solubility enhancing and/or purification tag and best promoter to maximize protein expression and purification. Such a vector construction/expression screening method using traditional restriction enzyme cloning techniques is highly labor intensive and potentially takes several weeks just to make every conceivable construct. The cassette-based method described herein makes it possible to assemble all the possible constructs in less than one day, either by doing the constructions on a one-by-one basis (i.e. one vector assembly reaction in one reaction/tube) or assembling several vectors in a single vessel and screening the pool of possible vectors in subsequent downstream processes. Either way, the time required to make and screen many different expression plasmids for a single target sequence would be greatly reduced and thus would give the end user a significant advantage over traditional vector construction methods.

Exemplary hosts include prokaryotic and eukaryotic cells, e.g., monera (unicellular and colonial—including the true bacteria [eubacteria] and cyanobacteria [blue-green algae]); protista (unicellular protozoans and unicellular & multicellular [macroscopic] algae with 9+2 cilia and flagella called undulipodia); fungi (haploid and dikaryotic [binucleate] cells, multicellular, generally heterotrophic, without cilia and eukaryotic (9+2) flagella [undulipodia]); plantae (haplodiploid life cycles, mostly autotrophic, retaining embryo within female sex organ on parent plant)' and animalia (multicellular animals, without cell walls and without photosynthetic pigments, forming diploid blastula). The various cassettes selected (e.g. the selectable marker cassette, the origin of replication cassette and the promoter cassette) should work in the host cell used.

In certain embodiments, the target cassette may comprise a coding sequence for a polypeptide or a regulatory RNA (e.g., a small RNA such as a miRNA or siRNA). In one embodiment, the assembly process may operably link a promoter to the coding sequence, thereby providing for transcription and possible translation of the coding sequence in a cell. In these embodiments, the functional cassettes may be different promoters, and the method results in a plasmid in which the coding sequence is operably linked to a selected promoter such that the coding sequence (if it encodes a polypeptide) is properly transcribed and translated into a polypeptide in a host cell. In these embodiments, the set of promoter cassettes may contain any set of different promoters, e.g., any combination of promoters that are active in bacterial cells, promoters that are active in mammalian cells, and promoters that are active in yeast cells, for example. A promoter cassette can be selected based on the target host cell.

In another exemplary embodiment, the functional cassettes may encode different N-terminal purification tags and the method results in a plasmid that encodes a fusion of the polypeptide encoded by the coding sequence and an N-terminal purification tag. Likewise, the functional cassettes may encode different C-terminal purification tags and the method results in a plasmid that encodes a fusion of the polypeptide and a C-terminal purification tag. The N-terminal purification tag or C-terminal purification tags may be, for example, an Arg-tag, B-tag (VP7 protein region of bluetongue virus), calmodulin-binding peptide, CAT (Chloramphenicol acetyltransferase), CBP (Cellulose-binding domains), Chitin-binding domain, c-myc-tag, DHFR (Dihydrofolate reductase), DsbA, FLAG-tag, Galactose-binding protein, GST (glutathione S-transferase), HAT-tag, His-tag, HSV-tag, KSI, lacZ (beta-galactosidase), lac repressor, maltose-binding protein (MBP), cNusA, Polyaspartic acid, Polyphenylalanine, S-tag, SBP-tag, Staphylococcal protein A, Streptococcal protein G, Strep-tag, Ubiquitin, T7-tag, T7gene10, thioredoxin, His-patch thioredoxin, trpE or DsbA, to name a few (Zhang et al., 1998, Protein Exp. Purif. 12: 159-165). Other useful tags will undoubtedly be discovered or created.

In some embodiments, the selecting step may include (i) selecting a first functional cassette from a first set of functional cassettes of the same function; and (ii) selecting a second functional cassette from a second set of functional cassettes of the same function (where the first and second sets of functional cassettes have different functions, where the one functional cassette is a set of promoters and the other is a set of purification cassettes or shuttle origins of replication). In these embodiments, the method may produce a plasmid that comprises the first functional cassette, the second functional cassette, the target cassette, the origin of replication cassette and the selectable marker cassettes.

Various implementations of the method are described below.

Figure 3:
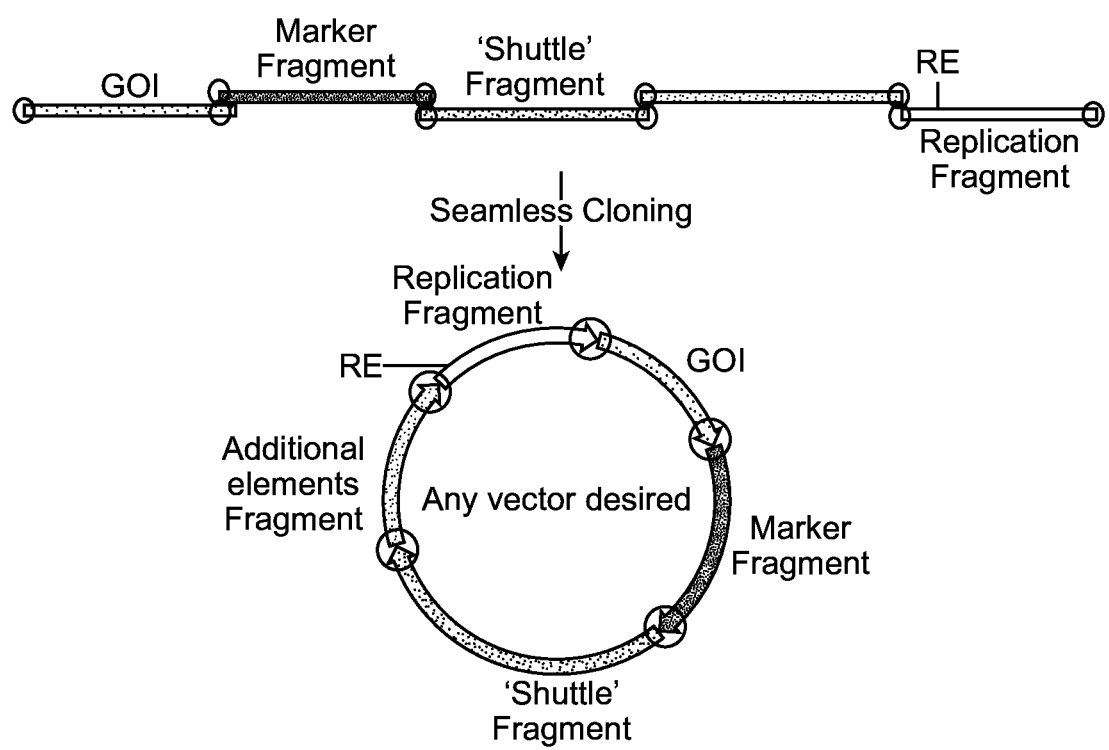
FIG. 3 schematically illustrates how a vector containing five cassettes can be assembled.

FIG. 3 below shows a vector design scheme, accentuating the complementary nucleotide sequences at the ends of adjacent cassettes (indicated by the circles) allowing assembly to occur. As mentioned above, the cassettes may include DNA sequences coding for origins of replication, selectable markers, "shuttle" sequences allowing plasmid transformation into a variety of organisms, promoters, ribosome binding sites, protein solubility and purification tags, to name a few. Cassettes are assembled in any order desired, as long as they possess complementary ends. Cassettes can be mixed together, subjected to in vitro linear amplification or other enzymatic treatment, followed by transformation into host cells where the final structure is converted into a functional plasmid construct in vivo.

Table 1 below illustrates the combinatorial flexibility of an exemplary kit that allows a wide variety of designs to be assembled and functionally tested in parallel, thus substantially reducing the time required for optimization employing conventional construction methods.

TABLE 1

Combinatorial nature of cassette-based construction method.

| Fragment | Number of Fragments | Fragment Examples |
|---|---|---|
| Gene of Interest (GOI) | 1 | End User Driven |
| Number of Origins of Replication | 2 | pUC, p15A, |
| Number of Selectable Markers | 4 | $Amp^R$, $Kan^R$, $Tet^R$ and $Chl^R$ |
| Number of Additional Elements | 2 | LacIq, T7 lyzozyme |
| 'Shuttle' Vector Fragments | 3 | Yeast, Mammalian, Strep |
| Total Number of Possible Vectors | 48 | |

FIGS. 4-10 provide examples of various ways of implementing the method described in general terms above.

Figure 4:
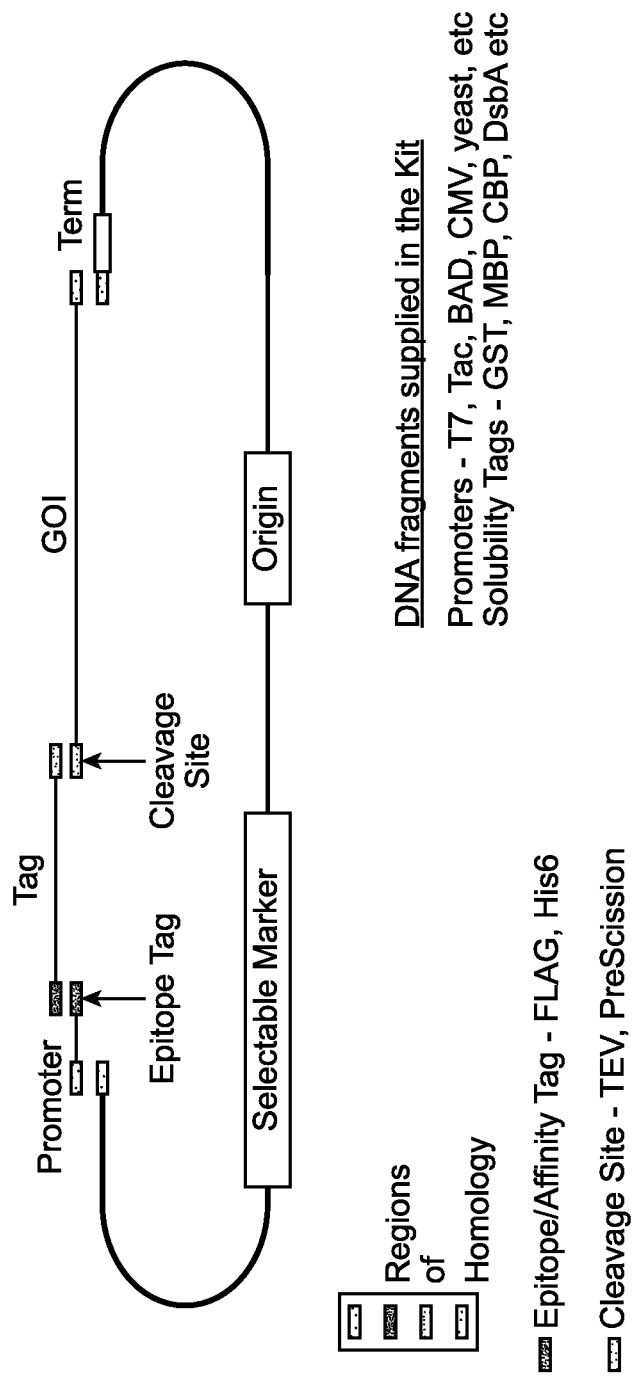
FIG. 4 shows some of the potential components of an exemplary protein expression vector construction kit (N-terminal purification tag).

FIG. 4 shows some of the components that could be used in a protein expression vector construction kit that uses an N-terminal purification tag. In the plasmid shown in FIG. 4, the target cassette (Gene of Interest (GOI)) can be ordered by the end user with the addition of the universal cloning sequences at the 5' end (cleavage site) and 3' end (a complementary region to the terminator). Alternatively, a gene or genes of interest could be generated by PCR using amplification primers containing the appropriate overlapping oligonucleotide sequences allowing multiple cassette assembly.

Figure 5:
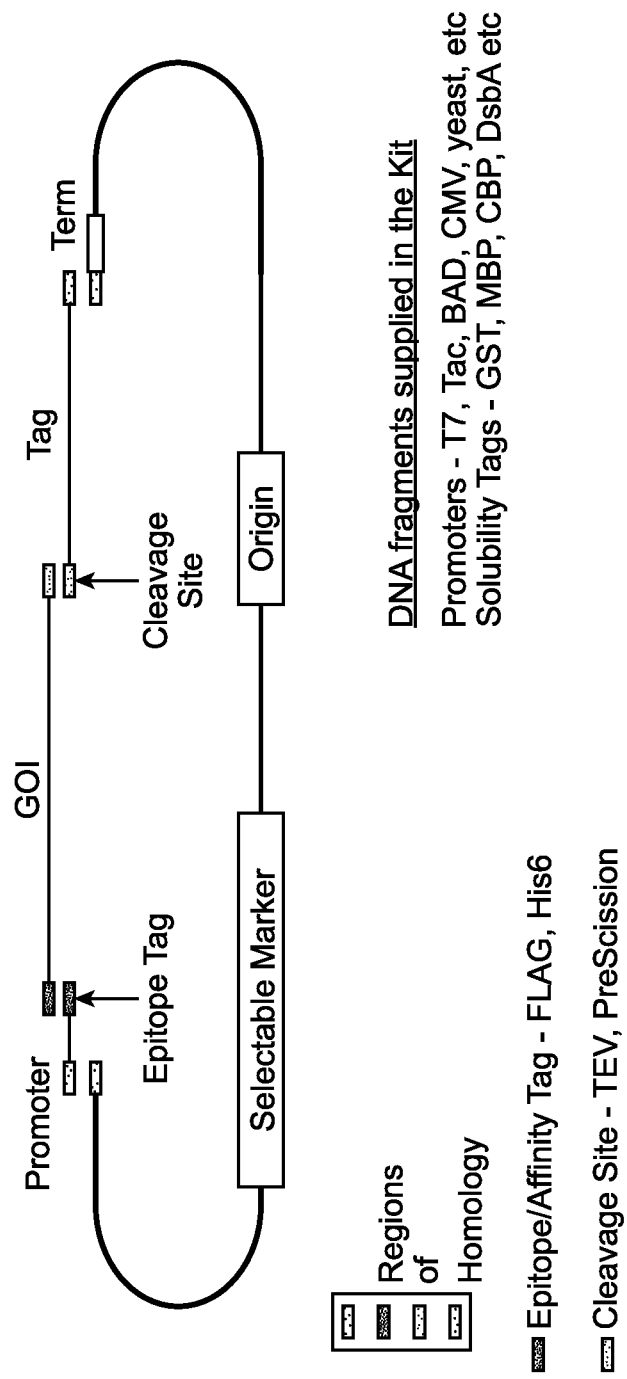
FIG. 5 shows some of the potential components of an exemplary protein expression vector construction kit (C-terminal purification tag).

FIG. 5 shows some of the components that could be used in a protein expression vector construction kit that uses a C-terminal purification tag. In the plasmid shown in FIG. 5, the target cassette can be ordered by the end user with the addition of the universal cloning sequences at the 5' end (cleavage site) and 3' end (a complementary region to the terminator).

Alternatively, a gene or genes of interest could be generated by PCR using amplification primers containing the appropriate overlapping oligonucleotide sequences allowing multiple cassette assembly.

Figure 6:
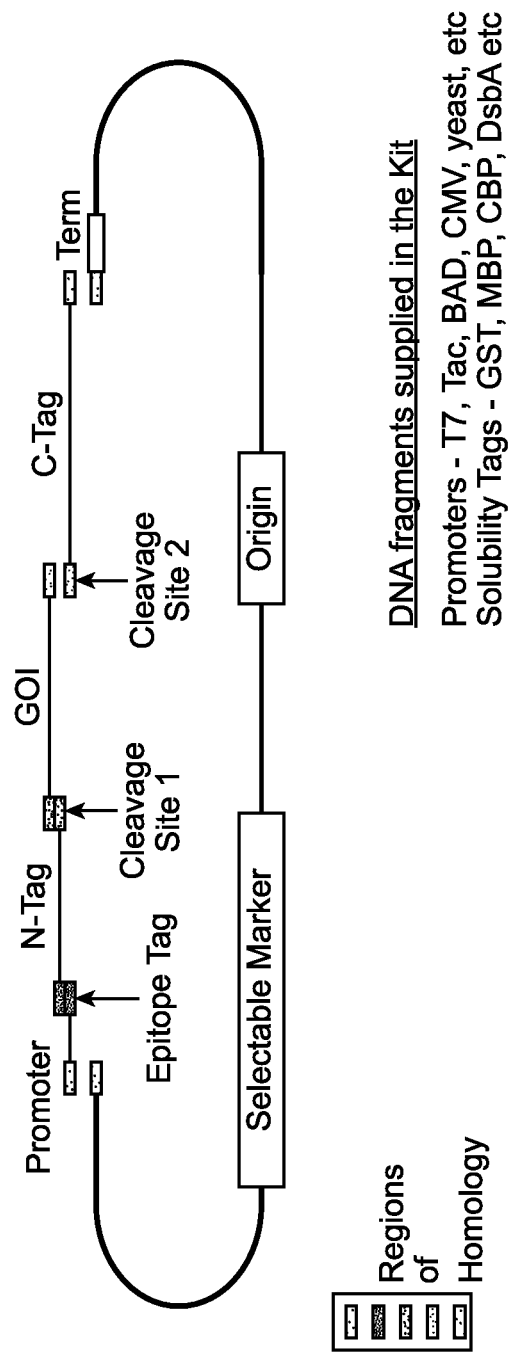
FIG. 6 shows some of the potential components of an exemplary protein expression vector construction kit (C-terminal purification tag and an N-terminal purification tag).

FIG. 6 shows some of the components that could be used in a protein expression vector construction kit that uses a C-terminal purification tag and an N-terminal purification tag. In the plasmid shown in FIG. 5, the target cassette can be ordered by the end user with the addition of the universal cloning sequence at the 5' end (cleavage site) and 3' end (a complementary region to the terminator). Alternatively, a gene or genes of interest could be generated by PCR using amplification primers containing the appropriate overlapping oligonucleotide sequences allowing multiple cassette assembly.

Figure 7:
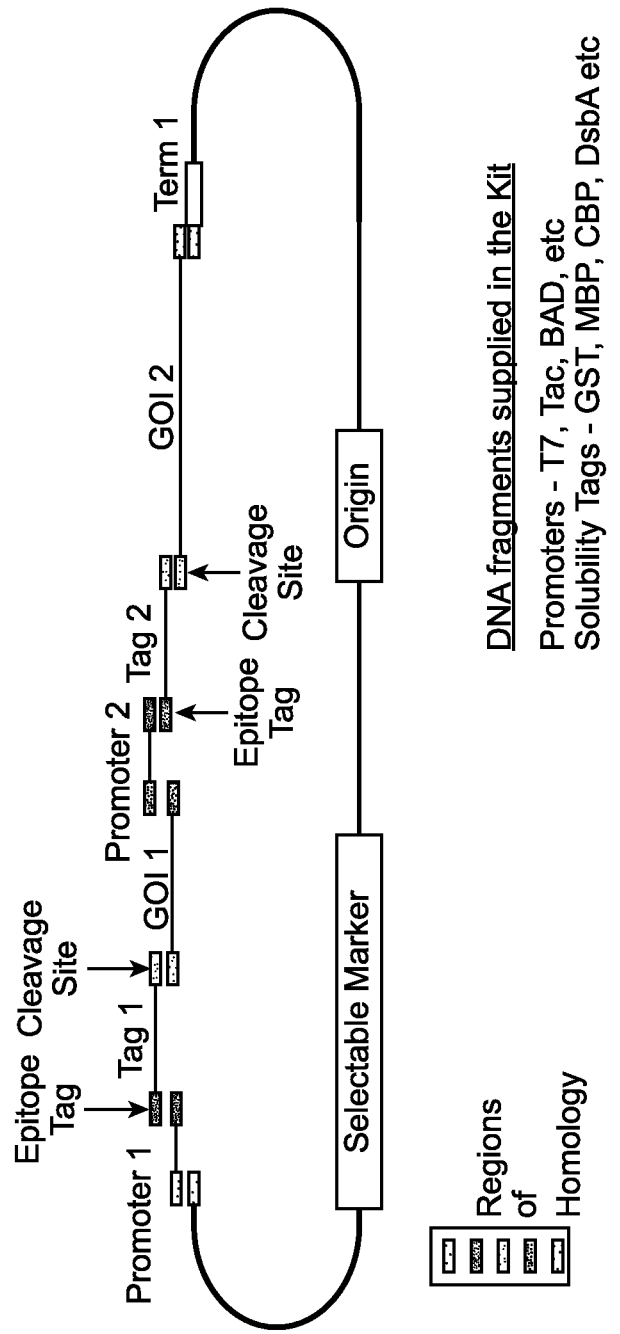
FIG. 7 shows some of the potential components of a exemplary kit that could be used to make a bicistronic vector.

FIG. 7 shows some of the components of a kit that could be used to make a bicistronic vector. In this illustration, the epitope/affinity Tag can also be the same protein sequence but different DNA sequence to avoid sequence conflicts. Also, the cleavage sites can be the same protein sequence but different DNA sequence to avoid sequence conflicts. The cleavage site may be Tobacco Etch Virus protease (TEV) and a variety of others. Alternatively, a gene or genes of interest could be generated by PCR using amplification primers containing the appropriate overlapping oligonucleotide sequences allowing multiple cassette assembly.

Figure 8:
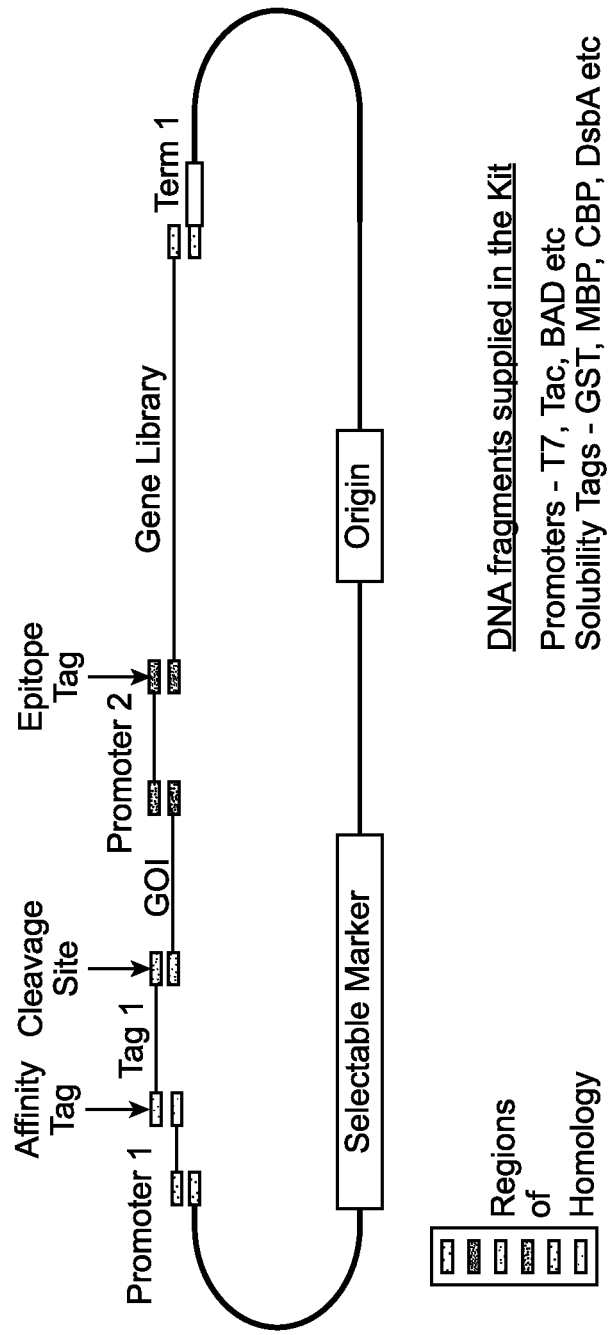
FIG. 8 shows the potential components of an exemplary kit that can be used to make a protein interaction screening vector.

FIG. 8 shows the components of a kit that can be used to make a protein interaction screening vector. In this illustration, the target cassette and gene library can be ordered by the end user with the addition of the universal cloning sequences at the 5' end and 3' end. The epitope/affinity tag can also be the same protein sequence but different DNA sequence to avoid sequence conflicts. Alternatively, a gene or genes of interest could be generated by PCR using amplification primers containing the appropriate overlapping oligonucleotide sequences allowing multiple cassette assembly.

Figure 9:
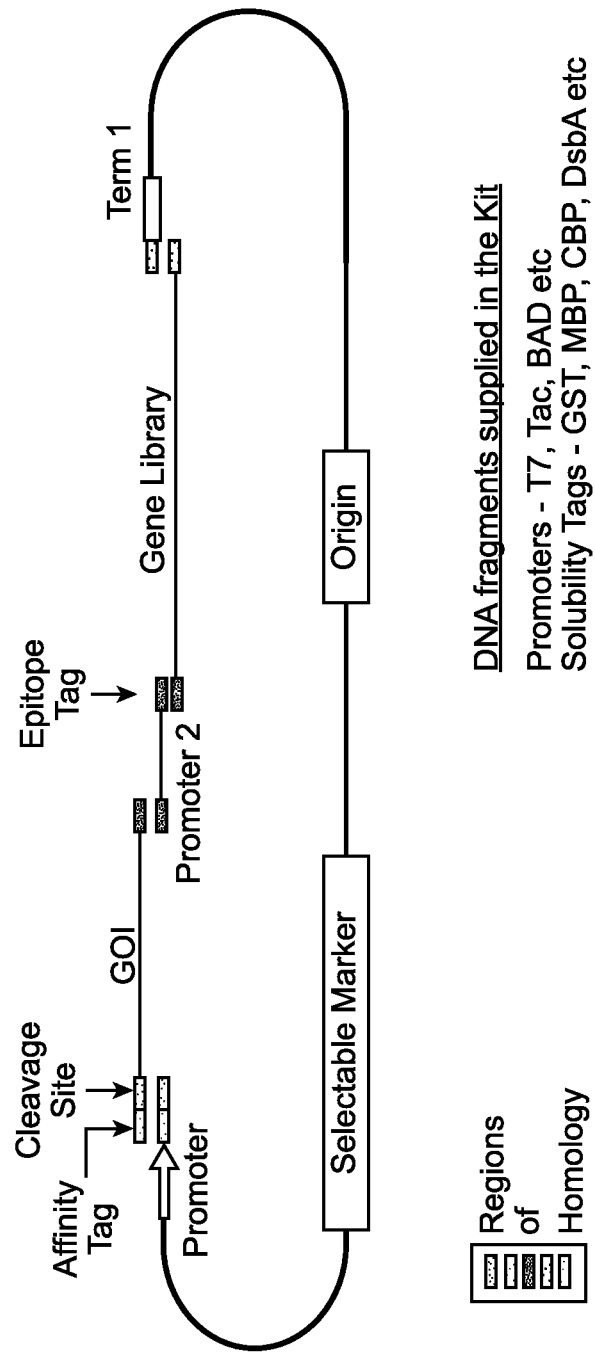
FIG. 9 shows the potential components of another kit that can be used to make a protein interaction screening vector.
Figure 10:
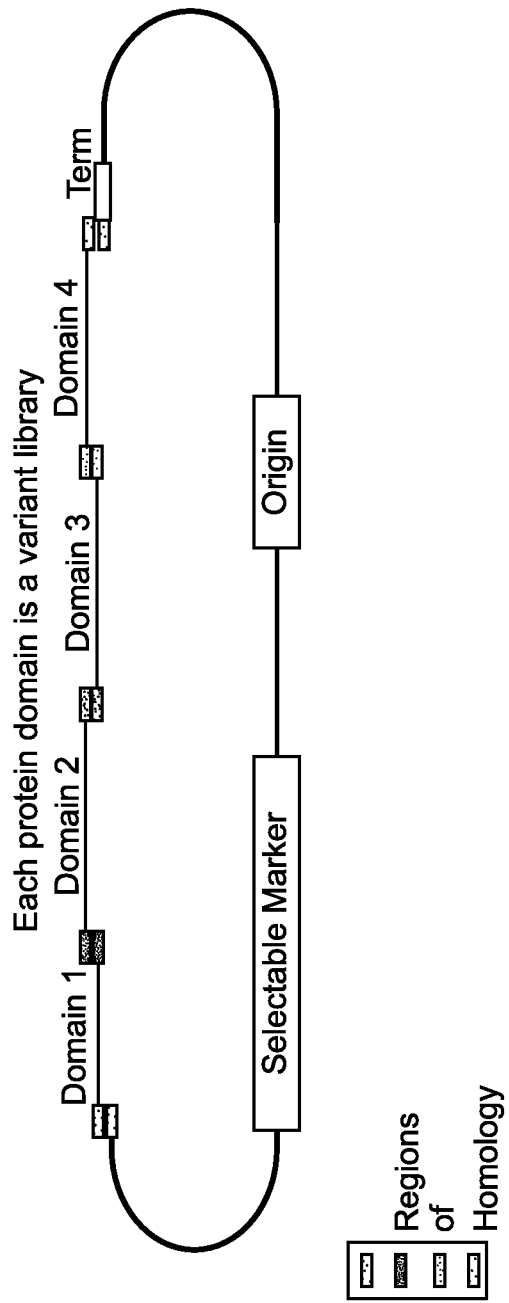
FIG. 10 shows how a library containing every possible combination of selected cassettes can be constructed.

FIG. 9 shows the components of another kit that can be used to make a protein interaction screening vector. In this illustration, the target cassette (GOI) and gene library can be ordered by the end user with the addition of the universal cloning sequences at the 5' end and 3' end. The Epitope/Affinity Tag can also be the same protein sequence but different DNA sequence to avoid sequence conflicts. Alternatively, a gene or genes of interest could be generated by PCR using amplification primers containing the appropriate overlapping oligonucleotide sequences allowing multiple cassette assembly. FIG. 10 shows the components of another kit that can be used to make vectors in which various regions are swapped. In one embodiment, a library containing every possible combination of cassettes is made and supplied to a user. The user can then screen the library to identify a clone of interest.

Kits

Also provided by this disclosure is a kit for practicing the subject method, as described above. A subject kit may contain at least a set of origin of replication cassettes; a set of selectable marker cassettes; one or more sets of functional cassettes; and a target cassette that comprises a sequence of interest; wherein the cassettes of each of the cassettes are in different vessels; and wherein hybridization of the target cassette with any of the origin of replication cassettes, any of the selectable marker cassettes, and any of the functional cassettes results in a product that can be introduced into host cells of interest. In certain cases, the kit may contain a first set of functional cassettes of the same function; and a second set of functional cassettes of the same function (where the first and second sets of functional cassettes have different functions, e.g., where is a set of promoters and the other is a set of purification cassettes or shuttle origins of replication). For example, the set of functional cassettes may comprise a set of different promoters that are active in bacterial cells, in mammalian cells, or in yeast cells, or a set of functional cassettes that comprise a set of cassettes that encode N-terminal or N-terminal purification tags. Further details of the cassettes that may be in a kit are described above. In addition to the cassettes, a kit may also contain reagents, e.g., buffers, enzymes and other necessary reagents, for performing the method described above. The various components of the kit may be present in separate containers or certain compatible components may be pre-combined into a single container, as desired.

In addition to the above-mentioned components, the subject kits may further include instructions for using the components of the kit to practice the subject methods and instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Some abbreviations are found in this disclosure: glutathione-S transferase (GST), maltose binding protein (MBP), cellulose binding protein (CBP), polymerase chain reaction (PCR), peptide nucleic acid (PNA), ribonucleic acid (RNA) and deoxyribonucleic acid (DNA). Other abbreviations are explained in the text.

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

EXAMPLES

Aspects of the present teachings can be further understood in light of the following examples, which should not be construed as limiting the scope of the present teachings in any way.

Example 1

Figure 11:
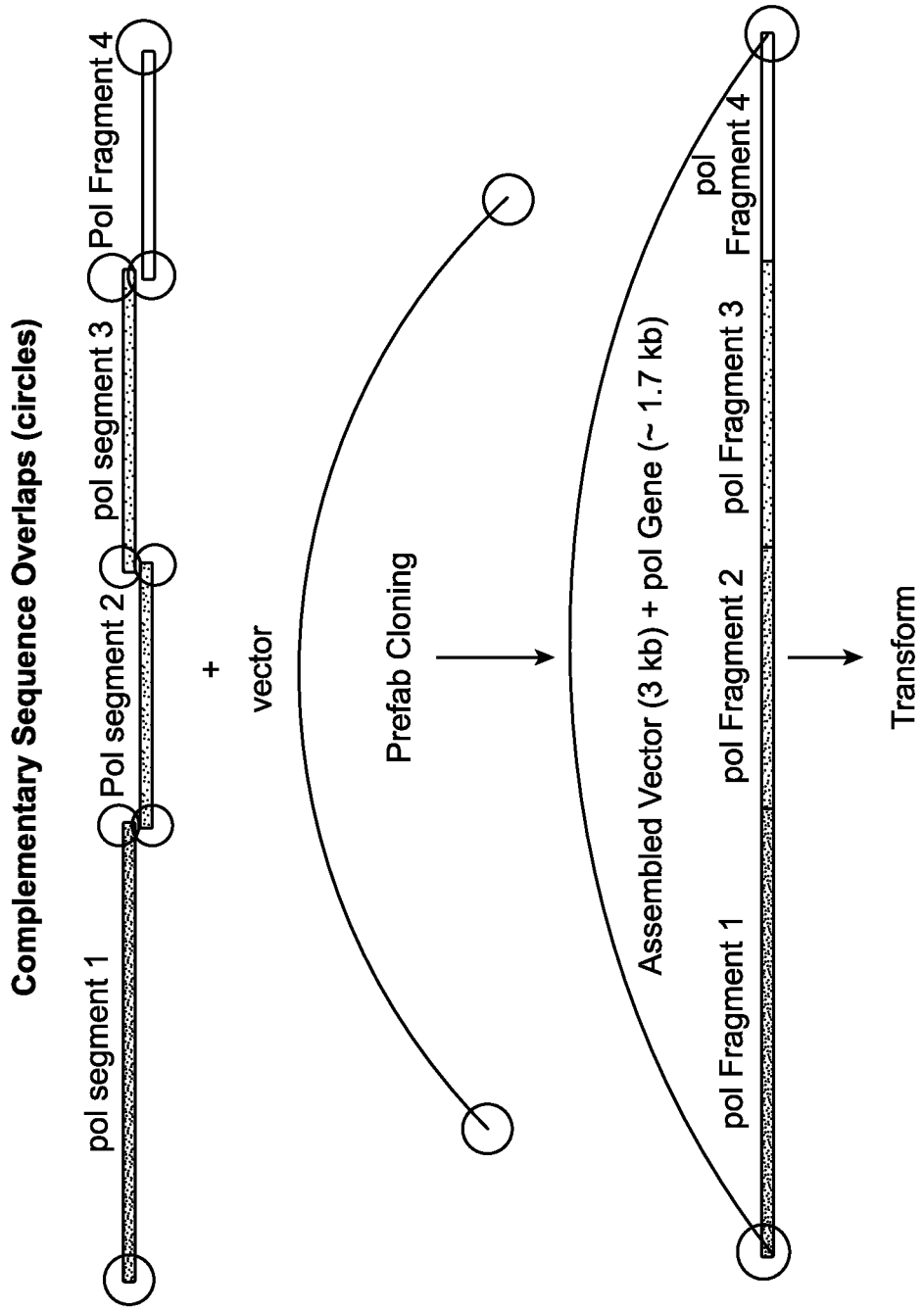
FIG. 11 shows the fabrication of a Pfu phage pol gene using a cassette assembly method.

A proof-of principle cassette assembly experiment was performed as follows. A *Pyrococcus furiosus* (Pfu) phage polymerase gene (pol) was divided into approximately four equal 500 nucleotide length segments by PCR. PCR primers were designed to amplify segment #1 with terminal sequences allowing it to anneal with the vector and segment #2. PCR primers for segment #2 allowed overlap between segment #1 and segment #3. PCR primers for segment #3 allowed overlap with segment #2 and segment #4. Finally, PCR primers were designed allowing segment #4 to overlap with segment #3 and the other end of the vector, as shown in FIG. 11. For this demonstration experiment, the individual polymerase segments were not purified. The vector was amplified so that the 5' and 3' ends contained sequences that overlapped with segments #1 and #4, respectively. The amplified polymerase segments and linear vector backbone were mixed in approximately equal molar ratios followed by linear amplification as described in Table 2.

TABLE 2

Linear Amplification Protocol.

| Step Number | Step Description | Temperature (° C.) | Number of Cycles |
| --- | --- | --- | --- |
| 1 | Initial Denaturation | 95° C. for 2 minutes | 1 |
| 2 | denaturation | 95° C. for 20 seconds | 15 |
| 3 | annealing | 60° C. for 20 seconds | |
| 4 | extension | 72° C. for 2.5 minutes | |
| 5 | Final Extension | 72° C. for 3 minutes | 1 |

Standard *E. coli* transformation procedures were followed and plated bacteria were incubated overnight at 37° C. Controls included eliminating segment #1 from one linear amplification reaction and eliminating all four segments in a separate linear amplification reactions. pUC 18 plasmid DNA served as a positive transformation control. Table 3 tallies transformed colonies from each reaction 1 through 4.

TABLE 3

Results of Transformation

| | Control Reaction | Number of Colonies | Number of Colonies Screened |
| --- | --- | --- | --- |
| 1 | Linear vector Only | 60 | 8 |
| 2 | Linear vector + 3 fragments | 35 | 8 |
| 3 | Linear vector + 4 fragments | 500+ | 16 |
| 4 | pUC18 (transformation control) | 500+ | NA |

Figure 12:
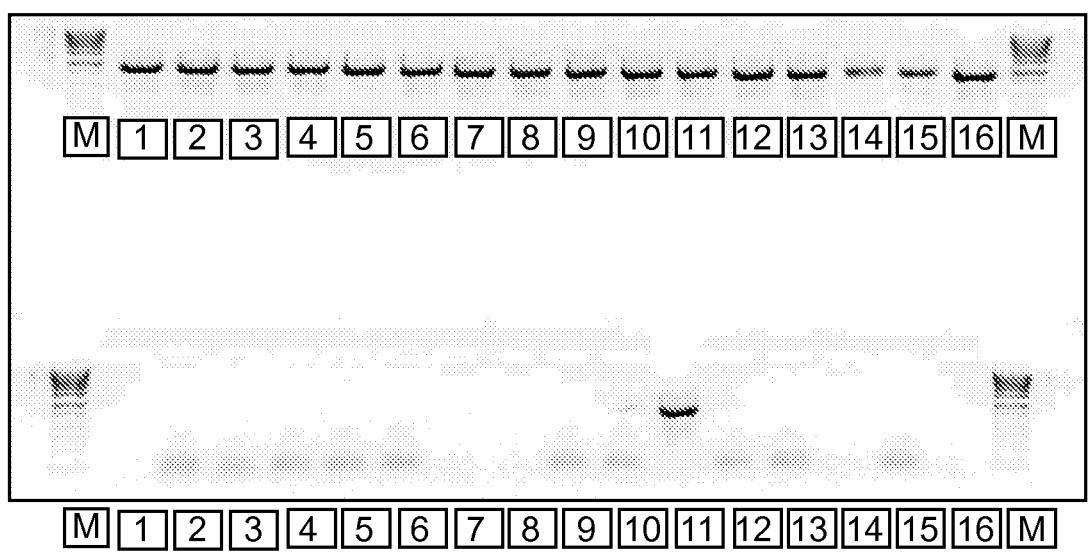
FIG. 12 shows the results of colony PCR of randomly picked clones. Lanes M–1 kb marker; Top row, lanes 1-16, correct size pol gene (4 pol fragments+vector; too many colonies to count); Bottom row, lanes 1-8 (no pol fragments+vector; 60 colonies); Bottom row, lanes 9-16 (three pol fragments+vector; 35 colonies).
Figure 13:
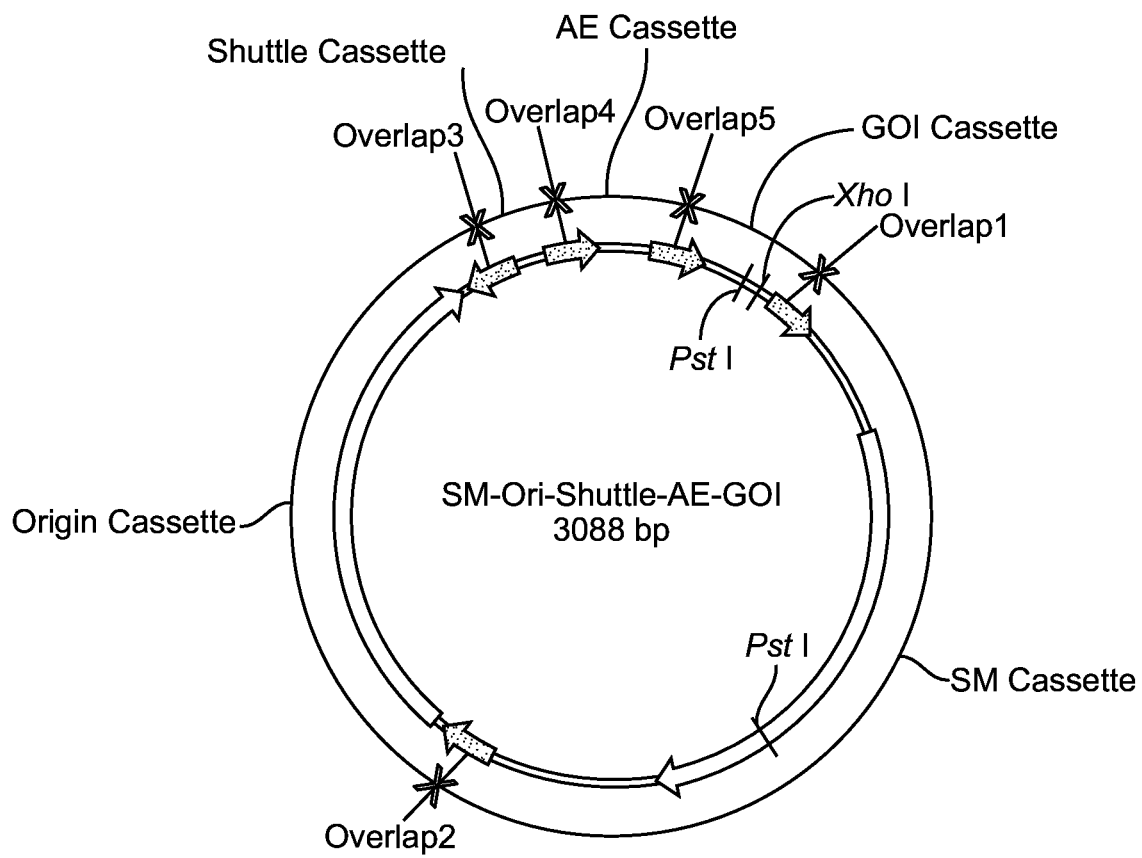
FIG. 13 is a schematic illustration of a proof of concept principle target vector.
Figure 14:
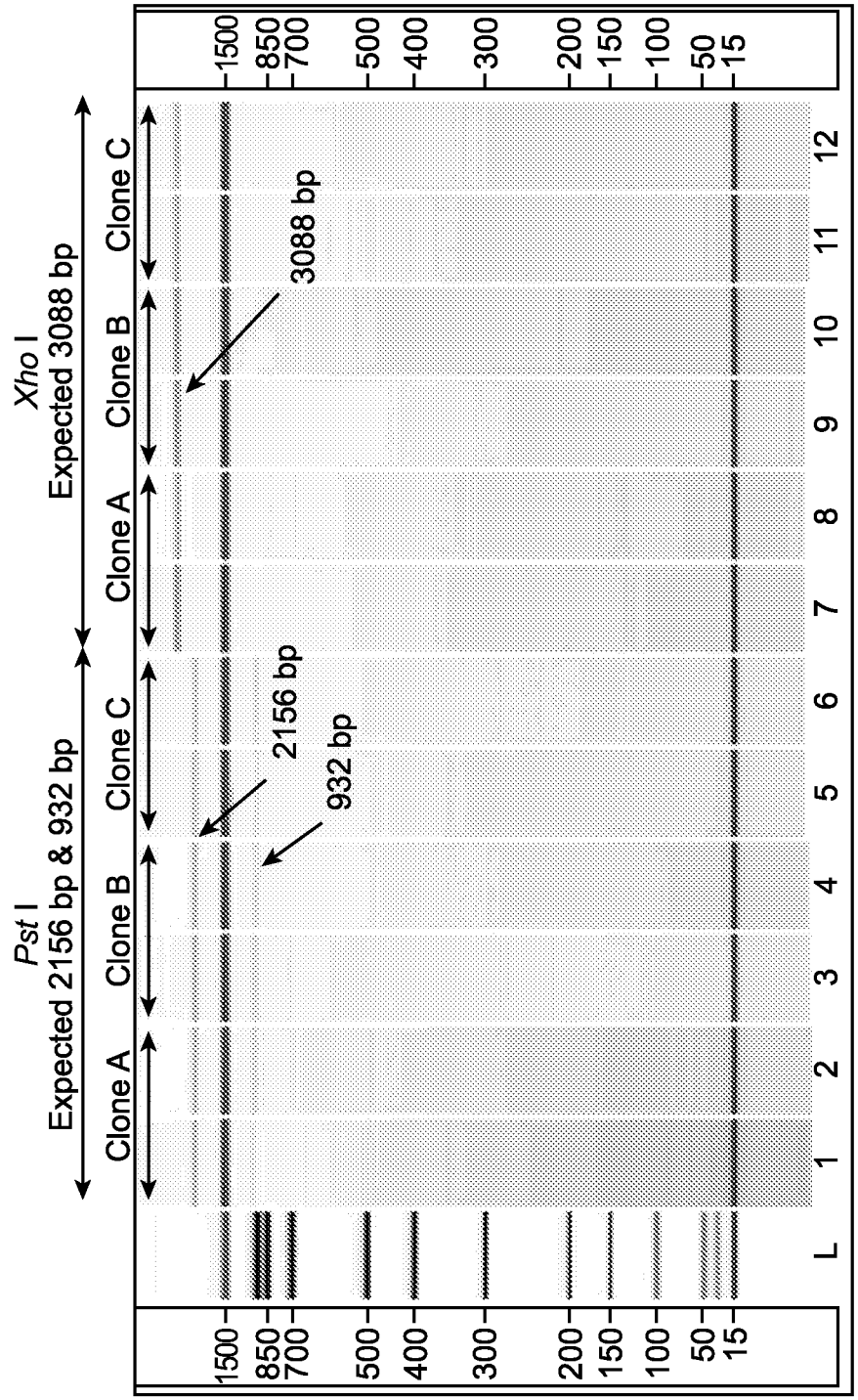
FIG. 14 shows a restriction digestion of proof of principle clones A, B and C.
Figure 15:
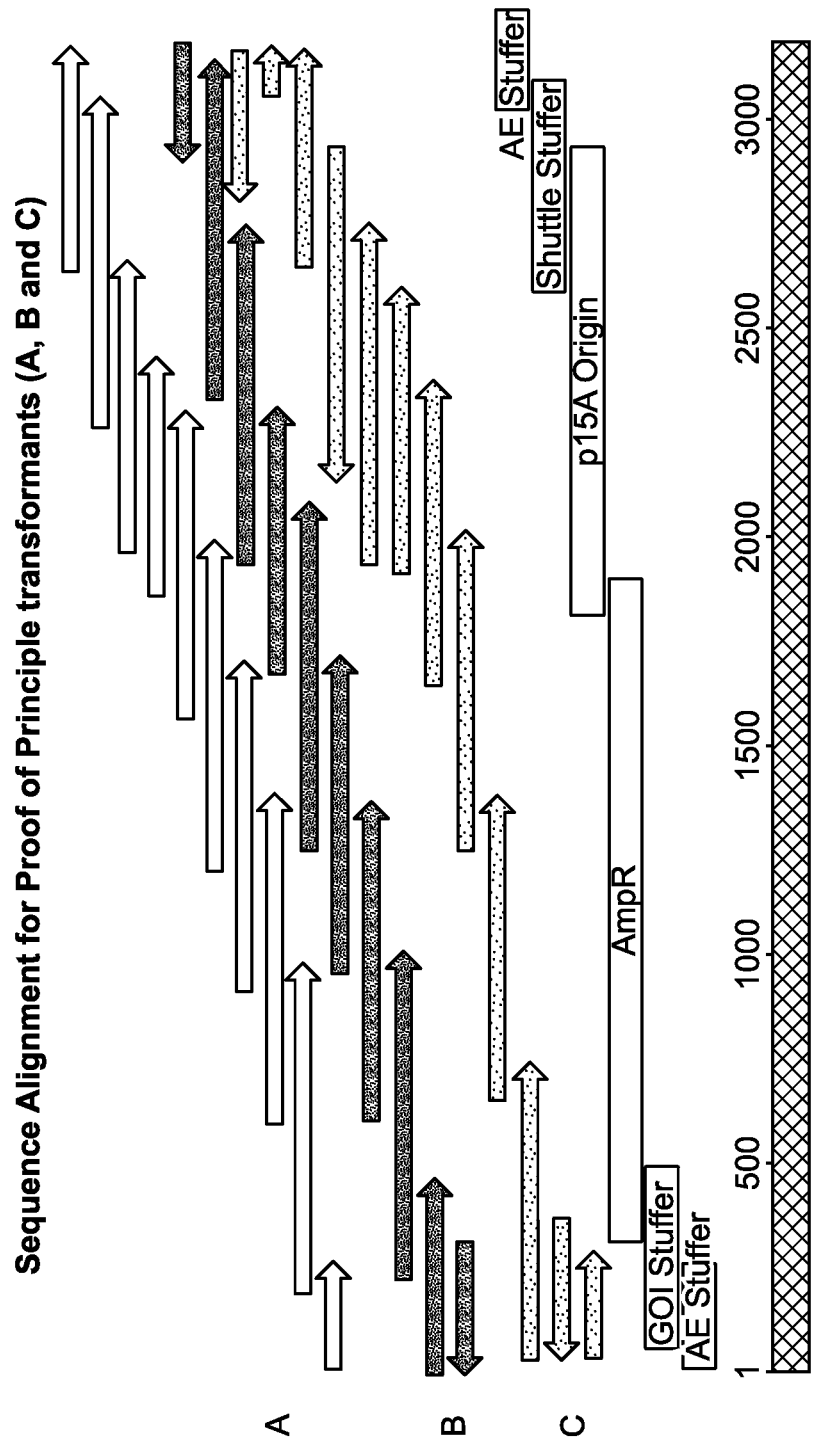
FIG. 15 shows a sequence alignment of proof of principle clones A, B and C.

Colony PCR was then performed on selected putative polymerase clones and reaction samples were run on an agarose gel to determine if inserts of the correct polymerase size were produced (FIG. 12). Inserts of the correct size were amplified from sixteen randomly chosen clones (reaction 3) resulting from transformation of reaction mixtures containing linearized vector and all four polymerase segments (top row, lanes 1-16). Bacterial colonies (sixty total) produced from transformation of reaction mixtures lacking all four segments (1) did not produce amplification products (bottom row, lanes 1-8). Bacterial colonies (thirty-five total) produced from transformation of reaction mixtures lacking segment #1 (2) produced one amplification product out of eight with a size approximately 500 bp smaller than the amplified inserts from clones containing all four polymerase segments (bottom row, lane 11 in the set 9-16). This result is partially explained by the fact that there were only three segments in this amplification reaction and not four.

Inserts from clones 1 and 16 (FIG. 12, top row) and clone 11 (FIG. 12, bottom row) were isolated and sequenced. Sequence data from clones 1 and 16 were identical to the authentic Pfu pol gene sequence. Examination of sequence from cloned insert 11 suggested that a blunt-end ligation reaction occurred between the free end of segment #3 and the free end of the vector.

Example 2

A proof-of principle vector assembly experiment was performed as follows: Five cassettes were created: a selectable Marker (SM) cassette (Ampicillin Resistance); an *E. coli* origin of replication cassette (p15A); a shuttle cassette; an Additional Element cassette and a GOI cassette Each cassette contained unique sequences at the 5' and 3' ends that were identical to the ends of the next cassette in the assembly work flow (i.e. SM-p15A-Shuttle-AE-GOI-SM) to create a 3088 bp circular plasmid as shown in FIG. 1.

For this proof of principle experiment, the individual cassettes were amplified by PCR and gel purified to eliminate any parental vector contamination in the final assembly reaction. The amplified cassettes were mixed in approximately equal molar ratios followed by thermocycling as described in Table 1. A control reaction only containing 4 of the 5 cassettes was also tested.

TABLE 1

Thermocycling Protocol.

| Step Number | Temperature (° C.) | Number of Cycles |
| --- | --- | --- |
| 1 | 95° C. for 2 minutes | 1 |
| 2 | 95° C. for 20 seconds | 5 |
| 3 | 64° C. for 30 seconds | |
| 5 | 4° C. | 1 |

Standard *E. coli* transformation procedures were followed and bacteria colonies were plated on agar plates containing ampicillin (50 μg/mL) and incubated overnight at 37° C. Table 2 records the number of recovered transformants from both reactions.

TABLE 2

Results of Transformation

| | Control Reaction | Number of Colonies | Number of Colonies Screened |
| --- | --- | --- | --- |
| 1 | 5 fragment Assembly | 3 | 3 |
| 2 | 4 fragment Control Assembly | 0 | 0 |

Restriction Digestion, with either Pst I and Xho I, was performed on the 3 putative clones and analyzed on a BioAnalyzer. All three clones gave the expected banding pattern for both restriction enzymes (FIG. 2). All three clones were completely sequence verified to confirm that all five cassettes had assembled in the expected order (FIG. 3). Subsequent assemblies using different batches of gel purified cassettes have confirmed this initial proof of principle result and have shown the process to be both robust and reproducible.

The invention claimed is:

1. A method for making a plasmid, comprising:
   (a) obtaining:
      (i) a set of origin of replication cassettes;
      (ii) a set of selectable marker cassettes;
      (iii) one or two or more sets of functional cassettes; and
      (iv) a target cassette that comprises a sequence of interest;
      wherein the cassettes in each of (i), (ii), (iii) and (iv) are in different vessels, and
      the cassettes are double stranded DNA molecules;
   (b) selecting an origin of replication cassette, a selectable marker cassette,
   and one or two or more functional cassettes from the sets of (a);
   (c) performing an assembly reaction with the cassettes selected in step (b) and said target cassette, wherein said cassettes comprise ends that hybridize with one another to produce a product that can be transformed or transfected into a host cell of interest, wherein the assembly reaction of the double stranded cassettes uses:
      (i) a DNA polymerase;
      (ii) a flap endonuclease; and
      (iii) a DNA ligase;
   (d) introducing the product of step (c) into a host cell; and
   (e) selecting a transformed or transfected host cell that harbors a plasmid that comprises said one or two or more selected functional cassettes, said target cassette, said origin of replication cassette and said selectable marker cassette.

2. The method of claim 1, wherein the one or two or more sets of functional cassettes are selected from:
   a set of promoter cassettes,
   a set of N-terminal purification tag cassettes,
   a set of C-terminal purification tag cassettes,
   a set of shuttle origin of replication cassettes,
   a set of terminator cassettes,
   a set of protein expression enhancer cassettes; and
   a set of shuttle selectable marker cassettes.

3. The method of claim 2, wherein said target cassette comprises a coding sequence for a polypeptide or a regulatory RNA.

4. The method of claim 3, wherein said functional cassettes are different promoters, and said method results in a plasmid in which said coding sequence is operably linked to a selected promoter.

5. The method of claim 4, wherein said selected promoter is active in prokaryotic or eukaryotic host cells.

6. The method of claim 3, wherein said functional cassettes encode different N-terminal purification tags and said method results in a plasmid that encodes a fusion of said polypeptide and an N-terminal purification tag.

7. The method of claim 3, wherein said functional cassettes encode different C-terminal purification tags and said method results in a plasmid that encodes a fusion of said polypeptide and a C-terminal purification tag.

8. The method of claim 1, wherein each end in step (c) hybridizes with one other end from a different cassette.

9. The method of claim 2, wherein said origin of replication cassettes are operable in prokaryotic and eukaryotic cells.

10. The method of claim 1, wherein said selecting step (b) comprises:
    (i) selecting a first functional cassette from a first set of functional cassettes of the same function; and
    (ii) selecting a second functional cassette from a second set of functional cassettes of the same function,
    wherein said method produces a transformable or transfectable product that comprises said first functional cassette, said second functional cassette, said target cassette, said origin of replication cassette and said selectable marker cassettes.

* * * * *